US009693945B1

(12) United States Patent
Sanders et al.

(10) Patent No.: US 9,693,945 B1
(45) Date of Patent: *Jul. 4, 2017

(54) METHOD OF SOLUBILIZING A COMPOSITION OF A CLEANED PHOTOCHROMIC DYE SUITABLE FOR USE ON HUMAN SKIN

(71) Applicants: Clifton Sanders, Carrollton, TX (US); Courtland Imel, Dallas, TX (US)

(72) Inventors: Clifton Sanders, Carrollton, TX (US); Courtland Imel, Dallas, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 15/449,929

(22) Filed: Mar. 4, 2017

Related U.S. Application Data

(63) Continuation-in-part of application No. 15/293,054, filed on Oct. 13, 2016, now Pat. No. 9,611,389, and (Continued)

(51) Int. Cl.
| | |
|---|---|
| *A61K 8/49* | (2006.01) |
| *C09B 57/00* | (2006.01) |
| *A61K 8/92* | (2006.01) |
| *A61K 8/37* | (2006.01) |
| *A61K 8/84* | (2006.01) |
| *A61K 8/81* | (2006.01) |
| *A61Q 17/04* | (2006.01) |

(52) U.S. Cl.
CPC .............. *A61K 8/498* (2013.01); *A61K 8/37* (2013.01); *A61K 8/4973* (2013.01); *A61K 8/8158* (2013.01); *A61K 8/84* (2013.01); *A61K 8/922* (2013.01); *A61Q 17/04* (2013.01); *C09B 57/00* (2013.01); *A61K 2800/434* (2013.01); *A61K 2800/45* (2013.01)

(58) Field of Classification Search
CPC .......... A61K 8/498; A61K 8/922; A61K 8/37; A61K 8/84; A61K 8/4973; A61K 8/8158; A61K 2800/45; A61K 2800/434; C09B 57/00; A61Q 17/04
See application file for complete search history.

(56) References Cited

U.S. PATENT DOCUMENTS

| 5,628,934 A | 5/1997 | Ohno et al. |
| 5,730,961 A | 3/1998 | Goudjii |
| | (Continued) | |

FOREIGN PATENT DOCUMENTS

| CN | 104068486 A | 10/2014 |
| CN | 104164151 A | 11/2014 |
| | (Continued) | |

*Primary Examiner* — Trevor Love
(74) *Attorney, Agent, or Firm* — Robert C. Klinger

(57) ABSTRACT

A method of solubilizing a composition, such as an organic manufactured photochromic dye that is free of carcinogens, non-mutagenic, non-toxic to human skin in any concentration, and suitable for application to, and absorbable by, human skin. The photochromic dye is suitable to be applied directly to human skin, and which dye is configured to indicate exposure to UV rays. The composition is configured to change color upon exposure to UVA, UVB and/or UVC rays. The composition can be used with other compositions, such as sunscreen, and be applied to human skin prior to application of the sunscreen, or, formulated with the sunscreen such that when the active ingredients of the sunscreen diminish, the photochromic dye will change color to generate a visual indicator of this condition.

16 Claims, 7 Drawing Sheets

Related U.S. Application Data a continuation-in-part of application No. 15/145,410, filed on May 3, 2016, now Pat. No. 9,545,374.

(56) References Cited

U.S. PATENT DOCUMENTS

| | | |
|---|---|---|
| 5,762,913 A | 6/1998 | Tanaka et al. |
| 5,986,273 A | 11/1999 | Tripp |
| 6,080,415 A | 6/2000 | Simon |
| 6,361,763 B1 | 3/2002 | Carroll |
| 6,461,594 B1 | 10/2002 | Chaiken |
| 6,470,891 B2 | 10/2002 | Carroll |
| 6,531,118 B1 | 3/2003 | Gonzalez |
| 7,022,331 B2 | 4/2006 | Theisen |
| 7,776,316 B2 | 8/2010 | Kolodziej et al. |
| 2002/0022008 A1 | 2/2002 | Forest |
| 2002/0192247 A1 | 12/2002 | Theisen |
| 2003/0030040 A1 | 2/2003 | Luthern |
| 2003/0226978 A1 | 12/2003 | Ribi |
| 2007/0183992 A1 | 8/2007 | Dumousseaux et al. |
| 2013/0240804 A1 | 9/2013 | Pagba |
| 2014/0187668 A1 | 7/2014 | Owen |

FOREIGN PATENT DOCUMENTS

| | | |
|---|---|---|
| CN | 104988766 A | 10/2015 |
| FR | 2845899 | 4/2004 |
| JP | 2006-022202 | 1/2006 |
| WO | WO 0203949 | 1/2002 |
| WO | WO 02078665 | 10/2002 |
| WO | WO 2016048426 | 3/2016 |

| Media Test Controls ||
|---|---|
| Media | Pass/Fail (circle one) |
| Negative control (w/ ethanol) | (Pass)/ Fail |
| Positive control | (Pass)/ Fail |
| Strain QC control | (Pass)/ Fail |

| Material/Sample(s) Evaluation | Yes | No | N/A |
|---|---|---|---|
| Was sample integrity considered compromised when received? | | ✓ | |
| Was the sample container visually examined prior to testing for any cracks, or damages? | ✓ | | |
| Did the sample appear homogenous? | ✓ | | |
| Was the sample submitted within the acceptable holding time? | ✓ | | |
| Were other samples tested at the same time? | ✓ | | |
| Were media and reagent used for the test within the expiration date? | ✓ | | |
| Have all testing components been purchased through approved vendors? | ✓ | | |
| Was the media early released? | | ✓ | |
| Did the media pass sterility and growth promotion quality control check? | | | ✓ |

| Personnel/Training | Yes | No | N/A |
|---|---|---|---|
| Did analyst possess and perform an adequate aseptic technique? | ✓ | | |
| Did the analyst wear proper PPE? | ✓ | | |
| Did the analyst perform an adequate hand sanitizing before and after test? | ✓ | | |
| Was the analyst effectively trained on the Method? | ✓ | | |
| Did the analyst complete the key method(s) for his/her proficiency training matrix? | ✓ | | |
| Did the analyst follow Standard Operating Procedure while performing test? | ✓ | | |
| Has the analyst ever performed this test previously? And successfully? | ✓ | | |
| Did any other samples result in an OOS that were tested by the same analyst? | ✓ | | |

| Equipment/Instrument | Yes | No | N/A |
|---|---|---|---|
| Was the equipment functioning properly during the test? | ✓ | | |
| Were all equipment/instruments (i.e. forceps, manifold, filter cup, pipette etc) used within their expiration date and calibration period? | ✓ | | |
| Did instrument meet performance criteria (i.e. Standard curve for LAL kinetic)? | | | ✓ |

FROM FIG. 4A

| | | | |
|---|---|---|---|
| Was proper pipette and pipette tips used for the test? | ✓ | | |
| Did hood cleaning perform before and after use of each test? | ✓ | | |
| Environment/Facility | Yes | No | N/A |
| Did weekly DI water testing meet acceptable criteria? | | | ✓ |
| Were Environmental results within specification? | | | ✓ |
| Were temperature monitoring performed accordingly to SOP? | ✓ | | |
| Are all the test controls, media controls data within specification? | ✓ | | |
| Were all controls performed concurrently with test? | ✓ | | |
| Method | Yes | No | N/A |
| Was the correct method used for testing? | ✓ | | |
| Was the sample tested according to the correct revision of the method? | ✓ | | |
| Was the sample validated for the method? | | ✓ | |
| Was the correct validation reference used? | | | ✓ |
| Was calculation performed correctly and dilution performed accordingly to the method? | ✓ | | |
| Micro Investigator's Conclusion | Yes | No | N/A |
| Is there assignable cause? | | ✓ | |
| Is there evidence of instrument error found? | | ✓ | |
| Is there analyst error found? | | ✓ | |
| Is result considered valid? | ✓ | | |
| Will there be a retest because of evidence of laboratory error? | | ✓ | |

Section VI - Quality Assurance

Initial Testing

All boxes must be checked prior to closing, indicating that there was no lab error.
- ☑ Analyst(s) trained in current procedure
- ☑ Equipment / Instruments within calibration
- ☑ All reagents approved/released for use/within expiry date
- ☑ All controls met specifications
- ☑ Trending data checked for testing performed

*QA Reviewer Conclusion*

Based on the investigation conducted the data, environmental monitoring readings, and media / test controls were within specification. There was no evidence of laboratory error detected throughout the investigation. The results obtained are considered valid and will be reported.

Experiment: AMES for GENE006

ACCESSION # ?

| ORGANISM | | NEGATIVE CTR | | | | POSITIVE CTR | | | | |
|---|---|---|---|---|---|---|---|---|---|---|
| | | Range | Count | Average | | Range | Count | Average | Pass/Fail | TA97a |
| TA97a | | without S9 | 104 | 98 | | without S9* | $(257/4) \times 57 = 3.7 \times 10^3$ | $3.5 \times 10^3$ | 35.7 | without S9 |
| | | without S9 | 91 | | | without S9* | $(232/4) \times 57 = 3.3 \times 10^3$ | | | without S9 |
| | | | | | | | | | Pass | without S9 |
| | | with S9* | $(110/4) \times 57$ | $1.6 \times 10^3$ | | with S9* | $(261/4) \times 57 = 3.7 \times 10^3$ | $3.6 \times 10^3$ | 2.1 | with S9* (86/4) |
| | | with S9* | $(121/4) \times 57$ | $1.7 \times 10^3$ | | with S9 | $(244/4) \times 57 = 3.5 \times 10^3$ | | | with S9* (89/4) |
| | | | Ave | | | | | | Pass | with S9* (102/4) |
| | | Range | Count | Average | | Range | Count | Average | Pass/Fail | TA98 |
| TA98 | | without S9 | 26 | 28 | | without S9* | $(59/4) \times 57 = 840$ | 530 | 18.9 | without S9 |
| | | without S9 | 29 | | | without S9 | 216 | | | without S9 |
| | | | | | | | | | Pass | without S9 |
| | | with S9* | $(43/4) \times 57$ | 610 | | with S9* | $(144/4) \times 57 = 2.1 \times 10^3$ | $2.3 \times 10^3$ | 2.7 | with S9* (105/4) |
| | | with S9* | $(79/4) \times 57$ | $1.1 \times 10^3$ | | with S9 | $(174/4) \times 57 = 2.5 \times 10^3$ | | | with S9* (83/4) |
| | | | Ave | 860 | | | | | Pass | with S9* (82/4) |
| | | Range | Count | Average | | Range | Count | Average | Pass/Fail | TA100 |
| | | without S9 | 91 | 77 | | without S9* | $(191/4) \times 57 = 2.7 \times 10^3$ | $2.2 \times 10^3$ | 28.6 | without S9 |
| | | without S9 | 63 | | | without S9* | $(118/4) \times 57 = 1.7 \times 10^3$ | | | without S9 |

FROM FIG. 5A

FIG. 5B

| | | Range | Count | Average | Range | Count | Average | Pass/Fail | | |
|---|---|---|---|---|---|---|---|---|---|---|
| TA100 | | | | | with S9* | (114/4)x57=1.6x10$^3$ | 1.5x10$^3$ | Pass | with S9 | |
| | | | | | with S9* | (95/4)x57=1.4x10$^3$ | | 12.5 | with S9 | |
| | | | | | | | | | | |
| TA102 | | Range | Count | Average | Range | Count | Average | Pass/Fail | TA102 | |
| | | without S9* | (45/4)x57 | 640 | without S9* | (88/4)x57=1.3x10$^3$ | 1.4x10$^3$ | Pass | without S9* | (43/4) |
| | | without S9* | (41/4)x57 | 580 | without S9* | (96/4)x57=1.4x10$^3$ | | 2.3 | without S9* | (53/4) |
| | | Ave | | 610 | | | | Pass | with S9* | (55/4) |
| | | with S9* | (83/12)x57 | 390 | with S9* | (85/4)x57=1.2x10$^3$ | 1.2x10$^3$ | | with S9* | (46/4) |
| | | with S9* | (107/12)x57 | 510 | with S9* | (78/4)x57=1.1x10$^3$ | | 2.7 | with S9* | (49/4) |
| | | Ave | | 450 | | | | Pass | with S9* | (44/4) |
| TA1535 | | Range | Count | Average | Range | Count | Average | Pass/Fail | TA1535 | |
| | | without S9* | (84/12)x57 | 400 | without S9* | (110/4)x57=1.6x10$^3$ | 1.7x10$^3$ | | without S9* | (105/12) |
| | | without S9* | (84/12)x57 | 400 | without S9* | (121/4)x57=1.7x10$^3$ | | 4.3 | without S9* | (80/12) |
| | | Ave | | 400 | | | | Pass | without S9* | (89/12) |
| | | with S9* | (93/12)x57 | 440 | with S9* | (133/4)x57=1.9x10$^3$ | 2.0x10$^3$ | | with S9* | (73/12) |
| | | with S9* | (85/12)x57 | 400 | with S9* | (138/4)x57=2.0x10$^3$ | | 4.8 | with S9* | (56/12) |
| | | Ave | | 420 | | | | Pass | with S9* | (79/12) |

Conclusion: Sample was found non-mutagenis to tester strains

METHOD OF SOLUBILIZING A COMPOSITION OF A CLEANED PHOTOCHROMIC DYE SUITABLE FOR USE ON HUMAN SKIN

CLAIM OF PRIORITY

This application is a continuation-in-part (CIP) of co-pending U.S. patent application Ser. No. 15/293,054 filed Oct. 13, 2016 entitled Method, Composition for the Preparation and Cleaning of Photo Chromic Dyes Resulting in a Product Suitable for Use on Human Skin, which is a continuation-in-part (CIP) of U.S. patent application Ser. No. 15/145,410 filed May 3, 2016, issued as U.S. Pat. No. 9,545,374 B2, entitled Method, Composition for the Preparation and Cleaning of Photo Chromic Dyes Resulting in a Product Suitable for Use on Human Skin.

TECHNICAL FIELD

The present disclosure relates to a method of solubilizing an organic manufactured photochromic dyes and inks, and a new manufacturing process that removes known carcinogens and toxins from organic manufactured photochromic inks and dyes. This process creates cleaned, solubilized non-mutagenic photochromic ink and dye materials suitable to be applied to and absorbed by human skin without causing adverse reactions, and which meet U.S. Federal Drug Administration (FDA) requirements.

BACKGROUND

Over eighty percent of the population will experience some type of reaction to their skin as a result of being exposed to Ultra Violet (UV) rays, such as UVA, UVB, and UVC rays. Such skin damage is photochemical in nature and is directly associated with high energy, short wavelength radiation. The end result is an undesirable biological change, such as inflammation and mutations to the DNA.

The use of photochromic dyes that illuminate with a wavelength between 200 nm and 600 nm serve as indicators to the public alerting them of their exposure to Ultra Violet rays.

The current manufacturing processes of photochromic dyes result in residual amounts of carcinogens remaining in, and on, these materials. By re-defining the manufacturing process, this disclosure provides a process to remove these carcinogens without altering chemical structure or function of the dyes.

These manufacturing processes are common throughout the industry for those companies manufacturing photochromic dyes. These photochromic dyes were not originally intended to be applied to human skin. Subsequently, there was no need to remove the affected carcinogens because the dyes and inks were used in other mediums (i.e. plastics, paper, t-shirts, and other novelty items).

SUMMARY

This disclosure provides a method of solubilizing a composition, such as an organic manufactured photochromic dye that is free of carcinogens, non-mutagenic, non-toxic to human skin in any concentration, and suitable for application to human skin. The photochromic dye is suitable to be applied directly to and absorbed by human skin, and which dye is configured to indicate exposure to UV rays. The composition is configured to change color upon exposure to UVA, UVB and/or UVC rays. The composition can be used with other compositions, such as sunscreen, and be applied to human skin prior to application of the sunscreen, or, formulated with the sunscreen such that when the active ingredients of the sunscreen diminish, the chromic dye will change color to generate a visual indicator of this condition.

BRIEF DESCRIPTION OF THE DRAWINGS

FIGS. 4A and 4B shows results from an Ames Out of Specification (OOS) test confirming the Ames test set-up of FIG. 3 is within Specification; and FIGS. 5A and 5B is a chart detailing actual Ames test results from cleaning a naphthopyran organic manufactured photochromic dye cleaned according to this disclosure, confirming the cleaned dye is free of carcinogens and is non-mutagenic

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Conventional and toxic organic manufactured photochromic dyes that include carcinogens are commercially available from numerous sources, such as Pittsburgh Paint and Glass of Pittsburgh, Pa. illustrative organic manufactured photochromic dyes include siro oxazines, which are blue dyes, and naphthopyrans that are yellow and red dyes. Because of the relative toxicity of these dyes when compared to other classes of dyes, they are more suitable for medical and skin usage. These dyes also have the advantage that they fade rapidly. One preferred photochromic dye is fused naphthopyrans with an alkyl bridge between the pyran rings.

Other conventional toxic and carcinogenic dyes that can be cleaned according to this disclosure include azobenzenes, photo fulgides, photochromic fulgides and diarylenthene. Photochromic fulgides and diarylenthene are fluorescing dyes.

Dyes are distinguished from pigments. A dye is a colored substance that has an affinity to the substrate to which it is being applied and can be absorbed by the substrate, and can be solubilized, such as in an ester. In contrast to a dye, a pigment is insoluble and has no affinity for the substrate. Dyes and pigments are distinct coloring substances. Dyes have significant advantages over pigments because dyes are absorbable in a substrate including human skin, and thus last longer that a topical pigment. In addition, pigments have a less vibrant color contrast, and are generally more expensive.

Conventional Cleaning Process for Photochromic Dyes

Figure 1A:
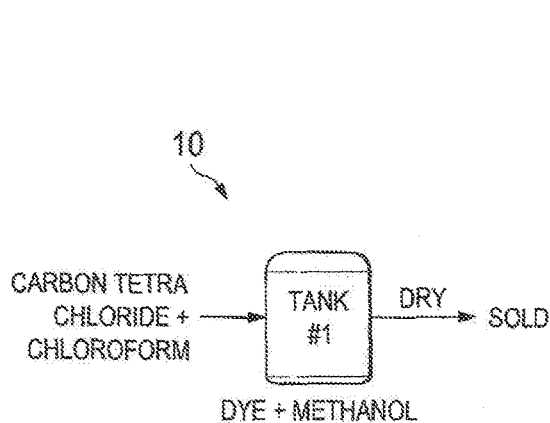
FIG. 1A is an apparatus.
Figure 1B:
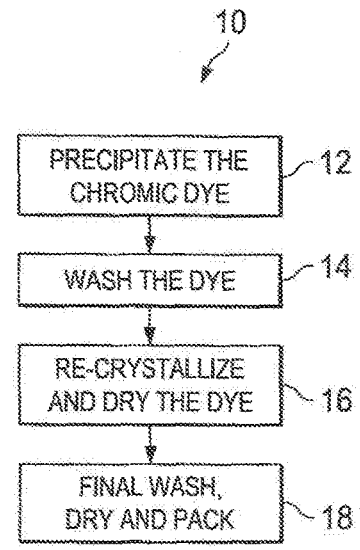
FIG. 1B is a conventional method for producing a photochromic dye that includes carcinogens using the apparatus of FIG. 1A.

Referring to FIGS. 1A and 1B, there is shown a conventional manufacturing process at 10 for processing a chromic dye that is toxic and contains carcinogens. Toxic dyes are defined in this disclosure as dyes that are toxic to human cells in any concentration. The conventional chromic dye is not suitable to be applied directly to human skin, but rather to, mediums such as plastics, paper, t-shirts, and other novelty items.

At step 12, the manufactured chromic dye is precipitated.

At step 14, the chromic dye is washed in a tank, also conventionally referred to as a reactor, in an equal portion of Carbon Tetra Chloride and Chloroform.

At step 16, the chromic dye is re-crystallized and dried in a rotary dryer.

At step 18, the chromic dye crystals are washed in 100% methanol, dried and packed.

Cleaning Process for Chromic Dyes Suitable for Human Skin

Figure 2A:
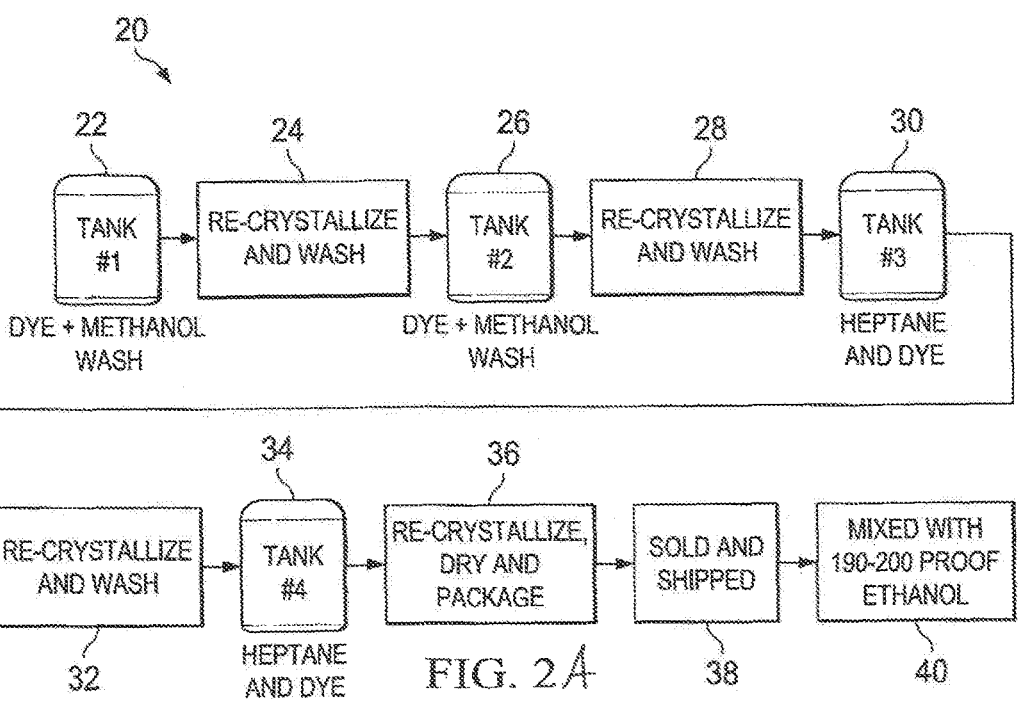
FIG. 2A is a diagram of a method for producing an organic manufactured non-toxic photochromic dye without carcinogens, and which can be directly applied to human skin for detecting exposure to UVA, UVB, and UVC rays.

Referring to FIG. 2A, there is shown one exemplary embodiment of a manufacturing process at 20 for producing a photochromic dye that is free of carcinogens, non-toxic and suitable for application to human skin, such as for use as a UVA, UVB and/or UVC indicator. The photochromic dye is configured to illuminate at a wavelength of between 200 nm and 600 nm, although other wavelengths are possible.

At step 22, the step of washing the photochromic dye in Carbon Tetra Chloride and Chloroform previously described in step 14 is removed entirely from the manufacturing process. The photochromic dye is washed in a first tank a first time with an alcohol based solution, such as in equal portions, preferably a 100% methanol wash in one exemplary embodiment. Ethanol Propanol can be used in another exemplary embodiment. The photochromic dye may be washed at room temperature in one illustrative embodiment. The photochromic dye may also be washed at 40 degrees Celsius to speed up the process in another illustrative embodiment. The wash process may last for 4 hours in one illustrative embodiment, but other longer and shorter times are acceptable. This step removes impurities that are harmful to human skin, such as toxins and carcinogens.

At step 24, the photochromic dye is re-crystallized and dried. In one illustrative embodiment, this may be done by vacuum filtering at room temperature. In another illustrative embodiment, the photochromic dye may be cooled at 25 degrees Celsius, for 4 hours to speed up the process. In an optional step, the re-crystallized dried dye is mixed in equal portions with a 45% Tolune, 45% Heptane, and 10% Ethanol solution, and then vacuum cooled again, such as at 25 degrees Celsius, for 4 hours to speed up the process. The wash process may last for 4 hours in one illustrative embodiment, but other times are acceptable.

At step 26, the re-crystallized and dried photochromic dye is washed in a second tank a second time in an alcohol based solution, such as in equal portions, preferably a 100% methanol wash in one exemplary embodiment, and Ethanol Propanol in another exemplary embodiment. The dye may be washed at room temperature in one illustrative embodiment. In another illustrative embodiment, the dye may be washed at 40 degrees Celsius to speed up the process. The wash process may last for 4 hours in one illustrative embodiment, but other shorter and longer times are acceptable. This additional wash is preferable, but not required if the wash of step 22 is sufficient to completely remove impurities that are harmful to human skin, such as toxins and carcinogens.

At step 28 the photochromic dye is re-crystallized and dried again. In one illustrative embodiment, this may be done by vacuum filtering at room temperature. In another illustrative embodiment, the dye may be cooled at 25 degrees Celsius, for 4 hours to speed up the process.

At step 30, the re-crystallized and dried photochromic dye is then washed a first time in an acyclic aliphatic solution, preferably 100% heptanes. The dye may be washed at room temperature in one illustrative embodiment. In another illustrative embodiment, the dye may be washed at 40 degrees Celsius to speed up the process. The wash process may last for 4 hours in one illustrative embodiment, although other longer and shorter times are acceptable. Acetone may be used in another exemplary embodiment. This wash in 100% heptanes is effective to completely remove impurities that are harmful to human skin, such as toxins and carcinogens.

At step 32 the photochromic dye is re-crystallized and dried again. In one illustrative embodiment, this may be done by vacuum filtering, such as at room temperature. In another illustrative embodiment, this may be done at 0 degrees Celsius, for 4 hours to speed up the process.

At step 34, the re-crystallized and dried photochromic dye is then washed a second time in an acyclic aliphatic solution, preferably 100% heptanes in one exemplary embodiment, and Acetone in another exemplary embodiment. In one illustrative embodiment, the dye may be washed for 4 hours at room temperature. In another illustrative embodiment, the dye may be washed at 40 degrees Celsius to speed up the process.

At step 36, the photochromic dye is re-crystallized and dried. In one illustrative embodiment, this may be done by vacuum filtering at room temperature. In another embodiment, this may be done at 0 degrees Celsius, for 4 hours to speed up the process.

The resulting recrystallized non-toxic photochromic dye is then packaged for sale and shipment, as depicted in step 38. In one illustrative embodiment, the dye may be vacuum packaged.

At step 40, upon receipt of the packaged non-toxic photochromic dye, and before formulation of the photochromic dye in a carrier, the photochromic dye is washed and solubilized in an ester of 190-200 proof ethanol to ensure that there is no trace of heptanes in the photochromic dye.

This process is safe, timely and cost effective.

In another exemplary embodiment, the photochromic dye can be washed only once in an alcohol based solution, such as only once in methanol or Ethanol Propanol, and only once in an acyclic aliphatic solution, such as 100% heptanes or Acetone. However, performing each wash twice helps ensure the production of the non-toxic photochromic dye suitable for application to human skin. In another exemplary embodiment, the photochromic dye may be washed more than once in an alcohol based solution, and more than twice in an acyclic aliphatic solution, such as 100% heptanes.

Solubility

The cleaned photochromic dye operates as a UV indicator, and can be formulated into a cosmetic base and applied safely on human skin. Other products, such as sunscreens, dermatology processes, anti-biotics, make-up and the like may be used with the cleaned photochromic dye.

The above described photochromic dye cleaning process 20 removes several unwanted solvents that aided in the mixing/solubility of the photochromic dye in many of cosmetic bases. Therefore, it is advantageous to create a cosmetic lotion, anhydrous, solvent marker, gel, and hydro alcoholic solution to improve the solubility of the cleaned photochromic dye for use in a cosmetic base.

Figure 2B:
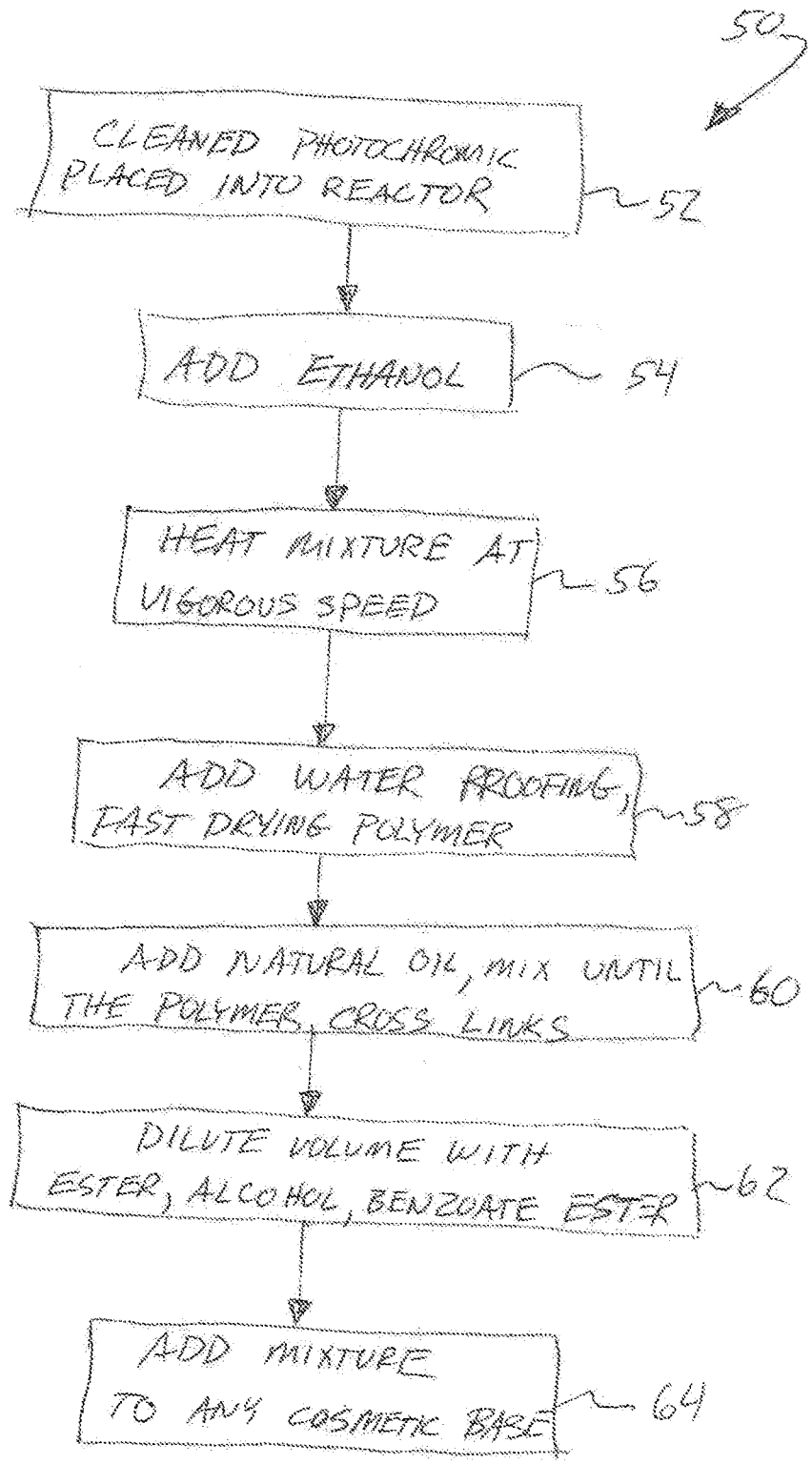
FIG. 2B is a diagram of a method for solubilizing the cleaned photochromic dye.

Referring to FIG. 2B, there is shown a process 50 for creating a cosmetic lotion, anhydrous, solvent marker, gel, and hydro alcoholic solution configured to improve the solubility of the cleaned photochromic dye as described above for use in a cosmetic base.

At step 52, a portion of the cleaned photochromic dye is placed in a clean reactor.

At step 54, an appropriate amount of an ethanol is added into the reactor to create a mixture. For example, a preferred mixture may be 50% of cleaned photochromic dye and 50% of ethanol. A desired concentration range of the mixture is 45% to 55% of cleaned photochromic dye, although other concentrations may be suitable.

At step 56, the mixture of step 54 is heated in the reactor at a vigorous speed to about 80 degrees Fahrenheit (F). The speed may be between 300 rotations per minute (RPM) and 800 RPMs until the cleaned photochromic dye is totally dissolved in the ethanol. The mixture can have a temperature of between 50 degrees F. and 100 degrees F.

At step 58, a water proofing, fast drying polymer or copolymer is added to the mixture of step 56 in the reactor. The amount of the polymer or copolymer may be 2-5% of the mixture after addition into the reactor. Suitable polymers include Styleze W-10 from ISP Technologies Inc. and Glossamer L-6600 from TRI K industries. The preferred polymer is Styeze W-10. This is a mixture of several materials. The next best preferred material is the Glossamer L-6600.

The polymer or copolymer is advantageous to form a waterproof film that contains the dissolved cleaned photochromic dyes.

At step 60, a natural oil, such as a castor oil, is added to the mixture of step 58 in the reactor, and the mixture is mixed until the polymer or copolymer cross links. The amount of natural oil is 3-5% of the mixture after addition into the reactor. This is advantageous to 4% to 5%.

At step 62, the mixture of step 60 is then diluted to a volume with an ester, such as an ethyl alcohol and/or C-12-15 benzoate alcohol ester. The mixture is then heated until all material has dissolved. Next, Dimethyl Isosorbide is added and mixed until the mixture is clear. The amount of Dimethyl Isosorbide is 3% to 7% of the mixture. This is desired to cross link the polymer or copolymer. This step completes the preparation of a solubilized cleaned photochromic dye.

At step 64, the solubilized cleaned photochromic dye of step 62 is added to a cosmetic base, such as a cosmetic lotion, anhydrous, solvent marker, gel, and hydro alcoholic solution. This creates a solubilized mixture of a cosmetic base and cleaned photochromic dye that will easily be absorbed into the skin of a mammal. This is because alcohol and Dimethyl Isosorbide penetrate the skin.

Figure 3:
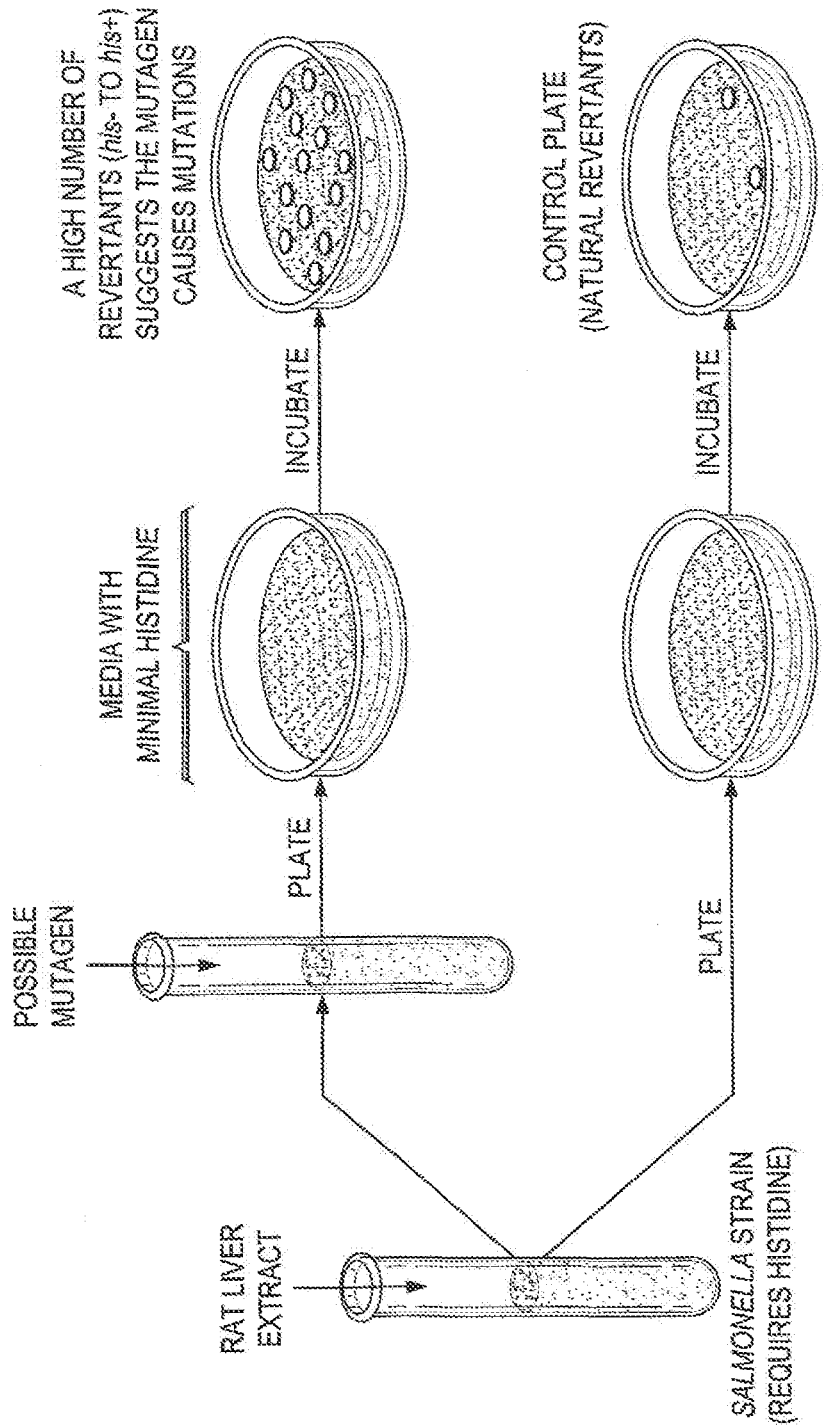
FIG. 3 is a layout of a set-up for conducting an Ames test that is commonly used to determine if a dye is free of carcinogens and non-mutagenic.

Referring to FIG. 3, there is shown a conventional layout of a set-up for performing an Ames test to determine if a dye has any carcinogens and if it is mutagenic. The Ames test is a widely employed method that uses bacteria to test whether a given chemical can cause mutation in the DNA of the test organism. More formally, it is a biological assay to assay the mutagenic potential of a chemical compound. A positive indicates that the chemical is a mutagenic compound and therefore may act as a carcinogen because cancer is often linked to mutations.

The Ames test uses several strains of the bacterium *Salmonella typhimurium* that carry mutations in genes involved in histidine synthesis. These strains are auxotrophic mutants, i.e. they require histidine for growth, but cannot produce it. The method tests the capability of the tested substance in creating mutations that result in a return to a "prototrophic" state, so that the cells can grow on a histidine-free medium.

The tester strains are specially constructed to detect either frameshift strains TA-1537 and TA-1538) or point (e.g. strain TA-1531) mutations in the genes required to synthesize histidine, so that mutagens acting via different mechanisms may be identified. Some compounds are quite specific, causing reversions in just one or two strains. The tester strains also carry mutations in the genes responsible for lipopolysaccharide synthesis, making the cell wall of the bacteria more permeable, and in the excision repair system to make the test more sensitive. Rat liver extract is optionally added to simulate the effect of metabolism, as some compounds, like benzo[a]pyrene, are not mutagenic themselves but their metabolic products are.

The bacteria are spread on an agar plate with small amount of histidine. This small amount of histidine in the growth medium allows the bacteria to grow for an initial time and have the opportunity to mutate. When the histidine is depleted only bacteria that have mutated to gain the ability to produce its own histidine will survive. The plate is incubated for 48 hours. The mutagenicity of a substance is proportional to the number of colonies observed.

Ames Test and Carcinogens

Mutagens identified via Ames test are also possible carcinogens, and early studies by Ames showed that 90% of known carcinogens may be identified via this test. Later studies however showed identification of 50-70% of known carcinogens. The test was used to identify a number of compounds previously used in commercial products as potential carcinogens. Examples include tris (2,3-dibromopropyl) phosphate, which was used as a flame retardant in plastic and textiles such as children's sleepwear, and furylfuramide which was used as an antibacterial additive in food in Japan in 1960s and 1970s. Furylfuramide in fact had previously passed animal test, but more vigorous tests after its identification in the Ames test showed it to be carcinogenic. Their positive tests resulted in those chemicals being withdrawn from use in consumer products.

One interesting result from the Ames test is that the dose response curve using varying concentrations of chemical is almost always linear, indicating that there is no threshold concentration for mutagenesis. It therefore suggests that, as with radiations, there may be no safe threshold for chemical mutagens or carcinogens. However, some proposed that organisms can tolerate low level of mutagens due to protective mechanisms such as DNA repair, and threshold may exist for certain chemical mutagens. Bruce Ames himself argued against linear dose-response extrapolation from the high dose used in carcinogenesis tests in animal systems to the lower dose of chemicals normally encountered in human exposure, as the results may be false positives due to mitogenic response caused by the artificially high dose of chemicals used in such tests. He also cautioned against the "hysteria over tiny traces of chemicals that may or may not cause cancer", that "completely drives out the major risks you should be aware of."

The Ames test is often used as one of the initial screens for potential drugs to weed out possible carcinogens, and it is one of the eight tests required under the Pesticide Act (USA) and one of six tests required under the Toxic Substances Control Act (USA).

Referring to FIGS. 4A and 4B, an Out Of Specification (OOS) test in accordance with Ames standards was performed on an Ames set-up according to FIG. 3, to qualify the set-up and validate the equipment used in the set-up as accurate and within Ames standard specifications. The data shown in FIGS. 4A and 4B verifies that the Ames set-up is within Specifications established by the Ames procedures.

Referring now to the chart in FIGS. 5A and 5B, there is shown detailed Ames test results of a cleaned naphthopyran photochromic dye according to the process of this disclosure using the qualified Ames set-up shown in FIG. 3. It can be seen that the Ames test results prove that the cleaned naphthopyran dye composition is non-mutagenic and free of carcinogens, and is non-toxic to human skin cells in any concentration.

Additional Ames tests of all disclosed photochromic dyes identified in previous paragraphs and cleaned according to the disclosed process show no residual carcinogens, that the cleaned photochromic dyes are non-mutagenic, and the cleaned photochromic dyes are non-toxic to human skin cells in any concentration.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

The invention claimed is:

1. A method of solubilizing a composition of an organic manufactured photochromic dye that is free of carcinogens, non-mutagenic, and configured to be absorbable by human skin, wherein the composition is made by a process that does not include any known carcinogens, comprising the steps of:
   1) adding a first quantity of the composition into a reactor;
   2) adding a second quantity of an ethanol into the reactor;
   3) adding a third quantity of a water proofing, fast drying polymer or copolymer into the reactor;
   4) adding a fourth quantity of a natural oil into the reactor to create a mixture; and
   5) diluting the mixture with an ester.

2. The method of claim 1 further comprising the step of adding Dimethyl Isosorbide to the mixture.

3. The method of claim 2 wherein the mixture is mixed until the mixture is clear.

4. The method as specified in claim 1 wherein step 4) is performed until the polymer or copolymer cross links.

5. The method as specified in claim 1 wherein the photochromic dye composition is configured to illuminate at a wavelength between 200 nm and 600 nm.

6. The method as specified in claim 1 wherein the photochromic dye is a naphthopyran.

7. The method as specified in claim 1 wherein step 2) includes mixing the composition and the ethanol at a vigorous speed until the cleaned photochromic dye is totally dissolved in the ethanol.

8. The method as specified in claim 6 wherein step 2) includes heating the mixed composition and the ethanol at a temperature of between 50 degrees F. and 100 degrees F.

9. The method as specified in claim 1 wherein the amount of the polymer or copolymer is 2-5% of the mixture after addition into the reactor.

10. The method as specified in claim 1 wherein the natural oil in step 4) comprises castor oil.

11. The method as specified in claim 1 wherein the ester in step 5) comprises an ethyl alcohol and/or C-12-15 benzoate alcohol ester.

12. The method as specified in claim 2 wherein the Dimethyl Isosorbide comprises 3% to 7% of the mixture.

13. The method as specified in claim 1 wherein the ethanol is at least 190 proof.

14. The method as specified in claim 1, wherein a concentration of the composition is between 45-55% when added to the ethanol in step 2).

15. The method as specified in claim 14, wherein the third quantity of the polymer or copolymer is in the range of 2-5% of the mixture after addition into the reactor.

16. The method as specified in claim 15, wherein the fourth quantity of the natural oil is in the range of 3-5% of the mixture after addition into the reactor.

* * * * *